CATAMENIAL TAMPON

Original Filed Nov. 12, 1969 2 Sheets-Sheet 1

Inventor.
Jacob A. Glassman
Elmer L. Gwickel
Atty.

CATAMENIAL TAMPON

Original Filed Nov. 12, 1969 2 Sheets-Sheet 2

Inventor.
Jacob A. Glassman
Elmer L. Gwickel
Atty.

United States Patent Office

Re. 27,677
Reissued June 19, 1973

27,677

CATAMENIAL TAMPON

Jacob A. Glassman, 1680 Meridian Ave.,
Miami Beach, Fla. 33139

Original No. 3,618,605, dated Nov. 9, 1971, Ser. No. 875,903, Nov. 12, 1969, which is a continuation-in-part of Ser. No. 800,983, Feb. 20, 1969. Application for reissue Dec. 22, 1971, Ser. No. 211,128
Int. Cl. A61f *13/20*
U.S. Cl. 128—270 7 Claims

Matter enclosed in heavy brackets [ ] appears in the original patent but forms no part of this reissue specification; matter printed in italics indicates the additions made by reissue.

ABSTRACT OF THE DISCLOSURE

A normally compacted tampon comprised of a laminated structure which embodies the arrangement of highly fluid absorbent layers that allow the menstrual wastes to be initially directed into a central absorbent core to thereby cause the core to expand and insure maximum expansion of the tampon as a whole so as to insure maximum absorption of the menstrual waste without outflow or strike-through, thus maintaining a blood-dry tampon exterior to the very end of its useful life.

This application is a continuation-in-part of my application Ser. No. 800,983, filed Feb. 20, 1969 and now U.S. Pat. No. 3,572,341.

The invention relates to improvements in catamenial tampons and is more particularly concerned with a critical arrangement of highly absorptive layers of material which, when compressed into tampon form and placed in use, will allow menstrual flow to be directed into the interior of the tampon, keeping the exterior surface substantially dry until the very end of its useful life. This tampon is also concerned with the presence therein of a novel expansible fluid-absorbent wad or core to insure maximum total expansion of its several layers of fluid-absorbent material. It also includes within its mass a layer of deodorant or hygienic medicinal impregnated gauze and a flow control layer of moisture impervious material which is perforated to allow for the controlled passage of waste fluids therethrough. The tampon, in one embodiment herein disclosed, incorporates a moisture barrier on its lower extremity to resist strike-through of waste fluids to the outside bottom thereof.

It is therefore an object of the invention to provide an improved catamenial tampon.

Another object is to provide a tampon critically fabricated of multiple-sized layers of fluid-absorbent material and including a layer of gauze impregnated with a deodorant or the like.

Another object is to provide a catamenial tampon with an innermost normally compressed highly expansible core of fluid-absorbent material.

Another object is to provide a tampon structure which possesses maximum absorptive properties and so constructed as to direct menstrual flow initially into the interior of the tampon.

Another object is to provide a caramenial tampon of the character referred to which, in the event of rapid flow of secretions, will allow its outer perforated area to direct the flow of fluids toward the center of the tampon to prevent sudden strike-through.

Another object is to provide a catamenial tampon of the character referred to which is not expensive or difficult to manufacture, and which is very effective in use.

Other objects and advantages of the invention will become apparent with reference to the following description and accompanying drawings.

Figure 2:
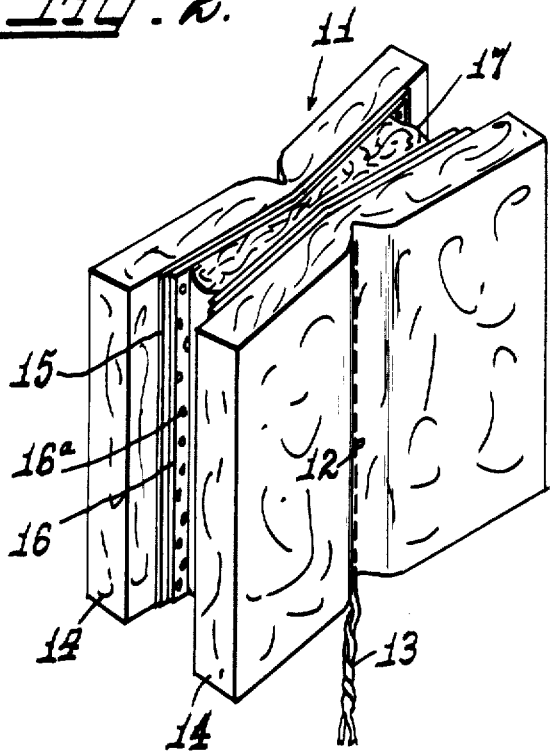
FIG. 2 is a perspective view of the tampon before it is compacted for insertion into the applicator tube.
Figure 1:
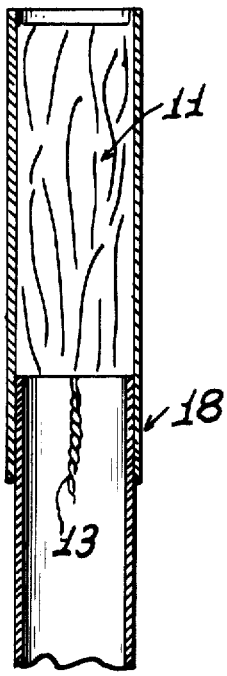
FIG. 1 is a view showing one embodiment of the tampon compacted and enclosed in an applicator tube, the latter being shown in section.
Figure 3:
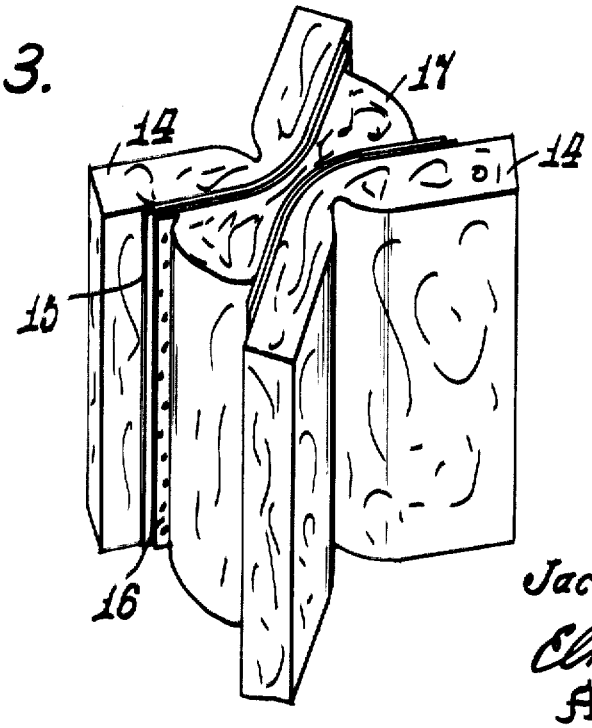
FIG. 3 is a perspective view similar to FIG. 2, showing the tampon expanded following absorption of menstrual fluids while in place in a vaginal passage.

Referring to the exemplary form of tampon illustrated in FIGS. 1 to 3, the tampon is fabricated from a substantially square laminated mass 11, having a longitudinal row of securing stitches 12 which terminates in a pull string 13. The mass 11 is comprised of outer layers 14 of cotton fibers each having on its inside face a layer of deodorant-impregnated gauze 15 overlaid with a sheet of moisture impervious material 16. Arranged between the opposed faces of sheet material 16 is a normally compressed wad or mass of moisture-absorbent material 17, such as cotton fibers. The sheets 16 are perforated, as at 16a, for a purpose to be explained presently. Preferably, the moisture impervious sheet 16 is less in width than the outer layers 14 and the wad 17 is less in width than the said sheet. The tampon is conventionally compacted into an applicator tube 18.

When the tampon is fitted into a vaginal passage, and menstrual fluids are being absorbed, there is substantial absorption by the centrally located compact mass 17; and also there is some fluid flow outwardly through the perforations 16a in sheets 16. The initial saturation by mass 17 causes said mass to expand thus spreading the overlying outer layers 14 so as to substantially fill out the vaginal passage. Subsequent discharge of menstrual fluids will result in said fluids being more readily absorbed by the outer absorbent layers 14 instead of bypassing the tampon. This structure thus insures maximum absorption of fluids by the tampon and extra safety by avoiding any premature spillover or flow through, soiling the underclothing.

Figure 4:
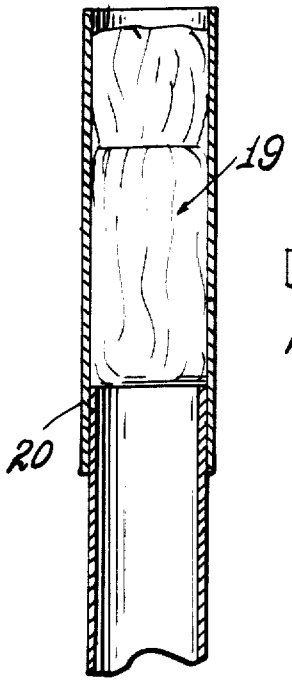
FIG. 4 is a view of another form of tampon showing it compacted within an applicator tube, the latter being shown in section.
Figure 5:
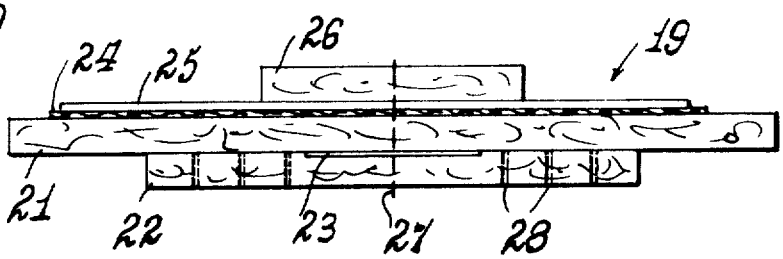
FIG. 5 is a side elevational view of the tampon of FIG. 4, prior to being shaped.

In the FIGS. 4 through 7 disclosure, a catamenial tampon 19 is formed from several varied size layers of material which are centrally sewn together so that when the layers are drawn up on all sides from the central area, a cup-shaped tampon is provided. Specifically, the tampon, which is commercially enclosed in a tubular applicator 20 as illustrated in FIG. 4, is comprised (FIG. 5) of a rather thick inner layer 21 of highly absorbent material, such as cotton fibers, and an outer underlying smaller size layer 22 of like material. The underlying layer 22, which constitutes the outside of the formed tampon, is substantially smaller in size than layer 21 so that the margins of the latter project appreciably beyond the edges of the former. If desired, a layer 23 of moisture impervious material, substantially smaller in size than the outer layer 22, may be situated between layers 21 and 22.

Arranged over the top face of layer 21, is a layer 24 of gauze, which is suitably impregnated with a deodorant or the like, and a covering layer 25 of moisture impervious material is laid over the gauze layer. A wad or mass 26 of highly absorbent material, [preferably] compressed, is placed over the moisture impervious layer 25 and the whole laminate assembly is secured into a unit by stitching 27 that is centrally located and which terminates in a pull string 27a.

Figure 6:
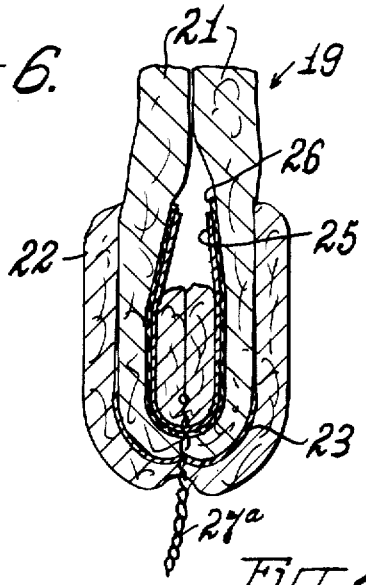
FIG. 6 is a central sectional perspective view of the FIG. 4 tampon, before it has absorbed any fluids and while still in its initially shaped condition.
Figure 7:
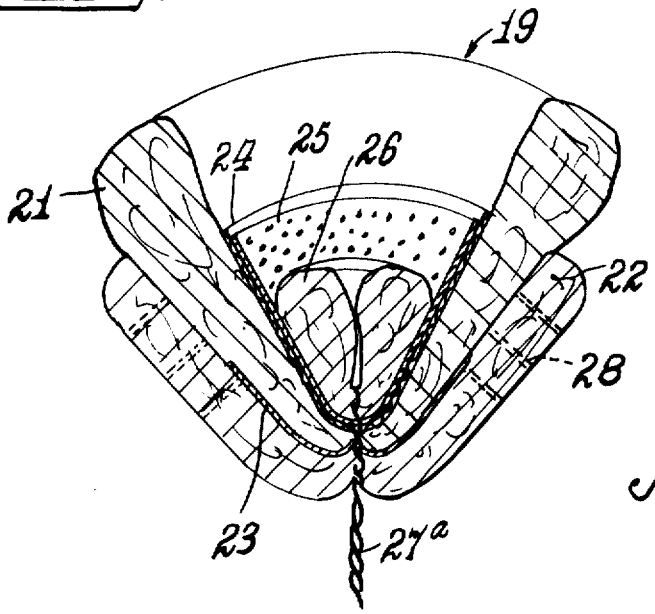
FIG. 7 is a view similar to FIG. 6, showing the tampon fully expanded within a vaginal passage and at least partially saturated with menstrual fluids.

In forming the tampon, the areas surrounding stitching 27 are drawn upwardly to enclose the mass 26 substantially into the condition shown in FIG. 6 wherein the opposed faces of the wad 26 and of the layer 21 are in substantial contact. It is in this condition when compacted to be inserted in the applicator and it initially remains in substantially this same general condition after being inserted into the vaginal passage. It should be especially noted that the margin of the inner absorbent layer 21 projects critically beyond all sides of the outer absorbent layer 22.

When inserted into the vaginal passage, the entry end of the tampon is first moistened sufficiently to spread apart and permit the menstrual fluids to enter directly into the interior wad or mass 26 which expands when saturated. Such expansion causes further outward expansion or opening of layers 21 and 22 to substantially fill the vaginal passage before there is any appreciable absorption of fluids by said layers. Even then there is no flow into the outer layer 22 until there is first a substantially total absorption of fluids by the inner layer 21. The structure and arrangement is such that the inner mass or wad 26 becomes substantially totally saturated before there is any flow of fluids through the perforated layer 25 to, and any material absorption of said fluids by, layer 21 and subsequently by outer layer 22. It is to be noted however, that the bottom region of the outer layer 22 is prevented from receiving any fluids directly from inner layer 21 by reason of the moisture impervious layer 23, thus premature strikethrough is avoided.

It may occasionally occur that a tampon lies at a sharp angle or almost horizontally while in the vaginal passage. In such event there is initially a deposit of menstrual fluids on the outside surface of the outer layer 22. In order to hasten the flow of such fluids into the interior of the tampon, and thus avoid early spillover, the outer layer 22 is formed with minute apertures 28 through which such fluids may flow rapidly into the adjacent inner layer 21 where they are absorbed and strike-through prevented.

Figure 8:
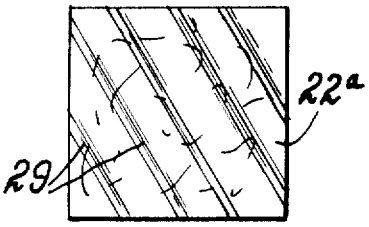
FIG. 8 is a bottom view of the outside layer of absorbent material showing a modified structure.

In the FIG. 8 disclosure, there is illustrated a form of outer layer 22a which is particularly suitable for this situation. Here the outside surface of said layer 22a is formed with angularly disposed channels or grooves 29 which have the effect of slowing down any direct tendency for the fluids to run straight down and off.

It should be evident that applicant has disclosed tampons that have maximum initial attraction for collecting waste fluids into their interior regions and which resist fluid absorption into their outer regions to thereby provide maximum external dryness and protection with no strike-through or spillage prior to total saturation by the entire tampon. In this manner the useful life of the tampon is prolonged without discomfort, premature feeling of wetness, or actual wetting of undergarments.

I claim:

1. A catamenial tampon comprising an outer layer of soft moisture-absorbent material, an inner layer of soft moisture-absorbent material overlying said outer layer, said inner layer being substantially larger than the outer layer so that its margins project beyond the edges of the outer layer in all directions, a highly compressed mass of fluid-absorbent material centrally located on the top side of the inner layer, said mass being substantially smaller than the inner layer, stitches joining said layers and mass in their central areas only, and the surrounding areas of the layers being gathered together to enclose the mass in a tubularlike formation with the inner layer projecting beyond the outer layer whereby said compressed mass upon being wetted will expand to spread the surrounding layers into a cup-shaped formation.

2. The tampon recited in claim 1, in which a layer of moisture-resistant material is arranged between the mass and the inner layer.

3. The tampon recited in claim 1, in which a perforated layer of moisture-resistant material is arranged between the mass and the inner layer.

4. The tampon recited in claim [1] *2*, in which a layer of medication-impregnated gauze lies between the moisture-resistant material and the inner layer.

5. The tampon recited in claim 1, in which a layer of moisture impervious material is arranged between the central areas of the inner and outer layers of absorbent material.

6. The tampon recited in claim [1] *5* in which the outermost layer of absorbent material is minutely and multiply perforated in the region of the impervious layer to allow rapid inflow from outside.

7. The tampon recited in claim 1, in which the outermost absorbent layer has fluid flow channels on its outside surface.

References Cited

The following references, cited by the Examiner, are of record in the patented file of this patent or the original patent.

UNITED STATES PATENTS

| | | | |
|---|---|---|---|
| 1,401,358 | 12/1921 | Peterkin | 128—285 |
| 2,330,257 | 9/1943 | Bailey | 128—285 |
| 2,499,414 | 3/1950 | Rabell | 128—285 |
| 2,508,214 | 5/1950 | Biederman | 128—285 |
| 2,998,010 | 8/1961 | Griswold et al. | 128—285 |
| 3,084,689 | 4/1963 | Maro et al. | 128—270 |
| 3,340,874 | 9/1967 | Burgeni | 128—285 |

CHARLES F. ROSENBAUM, Primary Examiner